United States Patent
Green

(10) Patent No.: US 9,457,511 B2
(45) Date of Patent: *Oct. 4, 2016

(54) SYSTEMS AND METHODS FOR UNIFORM EXPANSION AND HEAT SETTING OF MEDICAL DEVICES

(75) Inventor: Michael Lee Green, Pleasanton, CA (US)

(73) Assignee: ABBOTT CARDIOVASCULAR SYSTEMS, INC., Santa Clara, CA (US)

(*) Notice: Subject to any disclaimer, the term of this patent is extended or adjusted under 35 U.S.C. 154(b) by 594 days.

This patent is subject to a terminal disclaimer.

(21) Appl. No.: 13/490,266

(22) Filed: Jun. 6, 2012

(65) Prior Publication Data

US 2013/0327450 A1 Dec. 12, 2013

(51) Int. Cl.
 B29C 55/24 (2006.01)
 A61F 2/82 (2013.01)
 C22F 1/00 (2006.01)
 B29L 23/00 (2006.01)

(52) U.S. Cl.
 CPC .............. B29C 55/24 (2013.01); A61F 2/82 (2013.01); A61F 2240/001 (2013.01); B29L 2023/007 (2013.01)

(58) Field of Classification Search
 CPC ... B29C 55/24; A61F 2/82; A61F 2240/001; B29L 2023/007; C22F 1/00; B21D 31/04
 USPC ........................ 148/563; 264/234; 72/342.8
 See application file for complete search history.

(56) References Cited

U.S. PATENT DOCUMENTS

| | | | |
|---|---|---|---|
| 3,109,084 A * | 10/1963 | Walsh | ............................ 219/385 |
| 5,907,893 A | 6/1999 | Zadno-Azizi et al. | |
| 6,162,383 A | 12/2000 | Hane et al. | |
| 2013/0067907 A1* | 3/2013 | Greene et al. | ................... 60/527 |
| 2013/0160512 A1* | 6/2013 | Chen | ................................ 72/63 |
| 2013/0327113 A1* | 12/2013 | Green | .......................... 72/342.7 |

FOREIGN PATENT DOCUMENTS

WO   WO 2011/149598   12/2011

OTHER PUBLICATIONS

U.S. Appl. No. 14/860,402, Jul. 13, 2016, Office Action.

* cited by examiner

*Primary Examiner* — Jessee Roe
*Assistant Examiner* — Jenny Wu
(74) *Attorney, Agent, or Firm* — Workman Nydegger; John Kwok

(57) ABSTRACT

Systems and methods for uniformly expanding and heat setting medical devices. One method can include expanding a medical device by advancing the medical device over a preheated expander, the medical device being uniformly expanded as the medical device is advanced over the preheated expander; and heat setting the expanded medical device while the medical device is positioned over the expander, the preheated expander being maintained at a predetermined heat-setting temperature. The preheated expander can be positioned within a thermal chamber that maintains the preheated expander at the predetermined heat-setting temperature. The medical device can be physically separated from the preheated expander when the medical device is positioned over the expander and can be comprised of a shape-memory material. The preheated expander can remain heated during the expansion and heat setting of a plurality of medical devices.

16 Claims, 12 Drawing Sheets

SYSTEMS AND METHODS FOR UNIFORM EXPANSION AND HEAT SETTING OF MEDICAL DEVICES

BACKGROUND OF THE INVENTION

I. The Field of the Invention

The present invention generally relates to the field of medical devices. More specifically, the present invention relates to methods, systems, and devices for manufacturing a self-expanding medical device.

II. Related Technology

The use of intravascular devices to treat cardiovascular diseases is well known in the field of medicine. The need for a greater variety of devices to address different types of circumstances has grown tremendously as the techniques for using intravascular devices has progressed. One type of intravascular device is a stent or scaffold. Stents and scaffolds are generally cylindrically shaped intravascular devices that are placed within an artery (or other vessel within the body) to hold it open. The device can be used to reduce the likelihood of restenosis or recurrence of the blocking of a blood vessel and can be placed within an artery on a permanent basis, such as a stent, or a temporary basis, such as a scaffold. In some circumstances, a stent or scaffold can be used as the primary treatment device where it is expanded to dilate a stenosis and left in place.

A variety of stent and scaffold designs have been developed. Examples include coiled wires in a variety of patterns that are expanded after being placed within a vessel on a balloon catheter, helically wound coiled springs manufactured from expandable heat sensitive metals, stents or scaffolds shaped in zig-zag patterns, and self-expanding stents and scaffolds inserted in a compressed state for deployment in a body lumen.

Stents and scaffolds can have various features. For instance, a stent or scaffold can have a tubular shape formed from a plurality of interconnected struts and/or legs that can form a series of interconnected rings. In the expanded condition, the stent or scaffold can have a cylindrical shape to expand in an artery. One material for manufacturing self-expanding stents or scaffolds is nitinol, an alloy of nickel and titanium.

The conventional approach to manufacture a self-expanding stent or scaffold is to begin by laser cutting the design of the stent or scaffold from a tube having a diameter that is approximately equal to the desired diameter of the compressed (i.e., unexpanded) stent or scaffold. The tube is then deburred to clean any imperfections due to the cutting. Once the tube has been deburred, the tube is then expanded to the desired diameter, which is the diameter the stent will maintain when left within a body vessel. The tube is then heat set at the desired expanded diameter to maintain the tube at that diameter.

Conventionally, expanding the stent or scaffold to the desired expanded diameter requires an iterative process: The tube is positioned on a mandrel having a diameter that is slightly larger than the diameter of the compressed tube, thereby expanding the tube. Heat is applied to the tube while the tube is on the mandrel to heat set the tube at the new diameter. The tube and mandrel are allowed to cool to complete the heat setting, and the tube is then removed from the mandrel. This process is then repeated with a slightly larger mandrel to expand the tube further. This iterative process of expanding the tube a little at a time is repeated until the desired expanded diameter is attained.

Although the conventional manufacturing approach discussed above generally yields acceptable self expanding medical devices, the approach has some shortcomings. For example, it is cumbersome and time consuming due, in large part, to the iterative heating and cooling processes. In addition, a significant amount of energy is used by heating and reheating the medical device and the mandrel during each iteration. Another shortcoming is that, in many instances, cracks are induced in the stent or scaffold during conventional manufacturing due to undesired torque, tension, expansion, and/or compression.

BRIEF SUMMARY OF THE INVENTION

Embodiments of the invention relate to the manufacture of medical devices including implantable medical devices such as stents or scaffolds.

In one embodiment, a method of manufacturing a medical device can include expanding a medical device by advancing the medical device over a preheated expander, the medical device being uniformly expanded as the medical device is advanced over the preheated expander; and heat setting the expanded medical device while the medical device is positioned over the expander, the preheated expander being maintained at a predetermined heat-setting temperature.

In another embodiment, a method of manufacturing a medical device can include uniformly expanding a compressed medical device from a first diameter to a second diameter using a preheated expander; heat setting the expanded medical device at the second diameter while the medical device is positioned on the preheated expander; and removing the expanded medical device from the preheated expander, the steps of uniformly expanding the compressed medical device, heat setting the expanded medical device, and removing the expanded medical device all being performed while the preheated expander is maintained at a predetermined heat-set temperature.

In another embodiment, a method of manufacturing a medical device can include positioning a medical device on a plurality of transport mechanisms; advancing the transport mechanisms distally onto a preheated expander positioned within a thermal chamber, thereby causing the medical device to advance distally onto the preheated expander, the transport mechanisms acting as a bearing-type surface that supports and guides the medical device while maintaining a separation between the medical device and the preheated expander; and uniformly expanding the medical device while the medical device is positioned on the preheated expander, the medical device becoming heat set when expanded due to the preheated expander.

These and the other embodiments presented or envisioned herein provide significant benefits. One benefit is that the medical device can be expanded from the compressed size to a final desired size in a single step. That is, the medical device can be expanded to the final desired size using the systems and methods discussed and envisioned herein without going through an iterative expansion process. As a result, a significant amount of time can be saved using the inventive systems and methods compared to the conventional approach.

Another benefit is that the medical device expansion can occur while the expander mechanisms remain heated. That is, the medical device can be positioned on the expander mechanism, expanded, heat set, and then removed from the expander mechanism, all while the expander mechanism is maintained at the desired heat-set temperature. As a result, a significant amount of energy can be saved, as well as an additional amount of time that would otherwise be required to cool and then reheat the expander mechanisms, as is done in the conventional approach.

Another benefit is that frictional engagement between the medical device and the expander can be reduced or eliminated. As a result, the likelihood is reduced of damage to the medical device from excessive stresses caused by the expander during expansion of the medical device.

These and other advantages and features of the present invention will become more fully apparent from the following description and appended claims, or may be learned by the practice of the invention as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

DETAILED DESCRIPTION

As used in the specification and appended claims, directional terms, such as "top," "bottom," "up," "down," "upper," "lower," "proximal," "distal," and the like are used herein solely to indicate relative directions and are not otherwise intended to limit the scope of the invention or claims.

Systems and methods are provided herein for expanding a medical device. The methods provided through the system can allow the medical device to be expanded from the compressed size to a final desired size in a single step. That is, the medical device can be expanded to the final desired size using the systems and methods discussed and envisioned herein without going through an iterative expansion process. As a result, a significant amount of time can be saved using the inventive systems and methods compared to the conventional approach.

The inventive systems and methods can allow the medical device expansion to occur while the expander mechanisms, such as a mandrel, remain heated. That is, the medical device can be positioned on the expander mechanism, expanded, heat set, and then removed from the expander mechanism, all while the expander mechanism is maintained at the desired heat-set temperature. This can save energy, as well as an additional amount of time that would otherwise be required to cool and then reheat the expander mechanisms, as is done in the conventional approach.

The steps of the methods are repeatable and reduce the possibility of incorrectly expanding medical devices during the manufacturing process. The steps of the methods can be automated. Further, the methods provided herein can reduce the possibility of undesired torque, tension, expansion and compression of the medical device during manufacture.

Reference will now be made to figures wherein like structures will be provided with like reference designations. It is understood that the drawings are diagrammatic and schematic representations of exemplary embodiments of the invention, and are not limiting of the present invention, nor are they necessarily drawn to scale.

Figure 1:
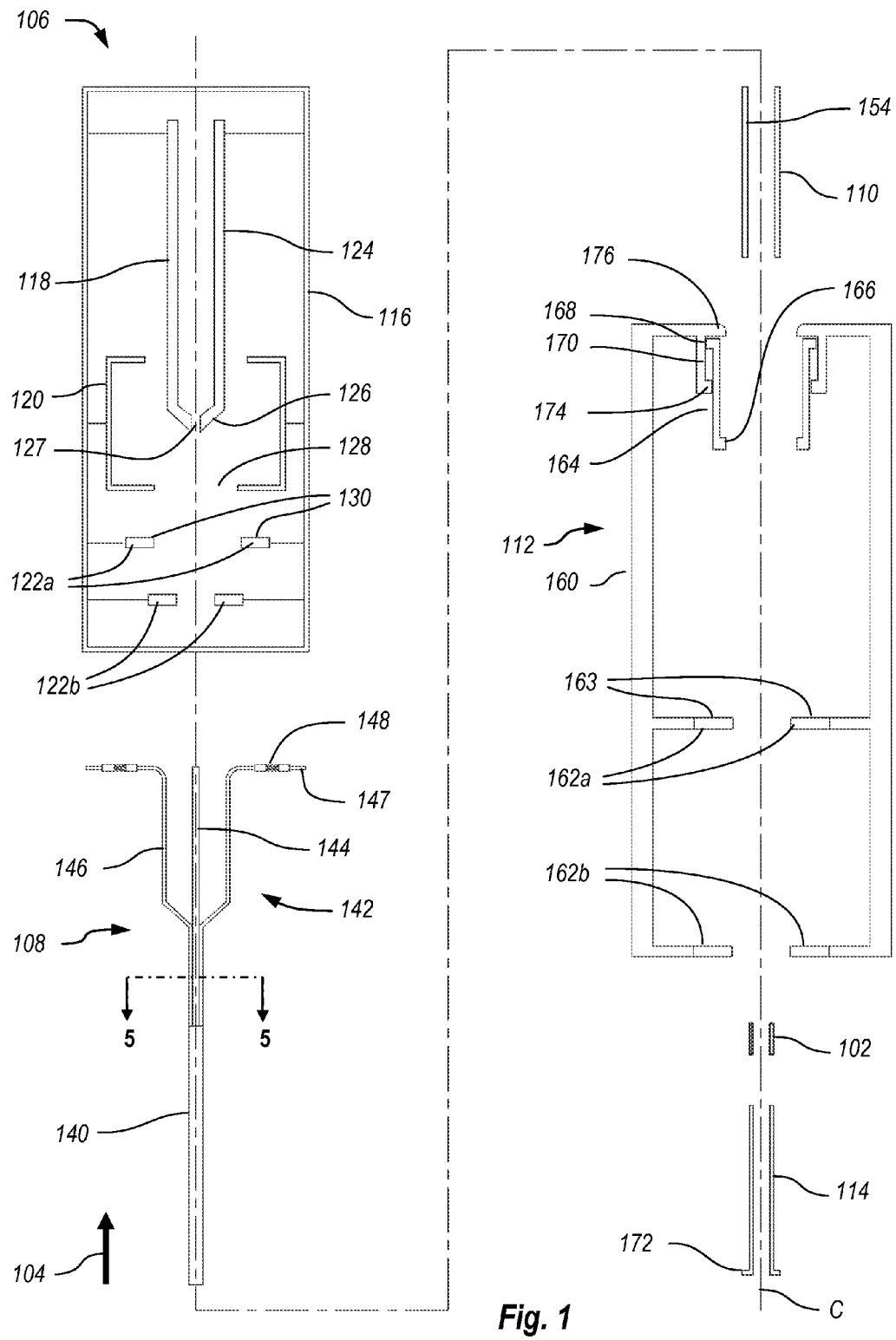
FIG. 1 illustrates an exploded view of a system for expanding a medical device according to one embodiment.
Figure 2:
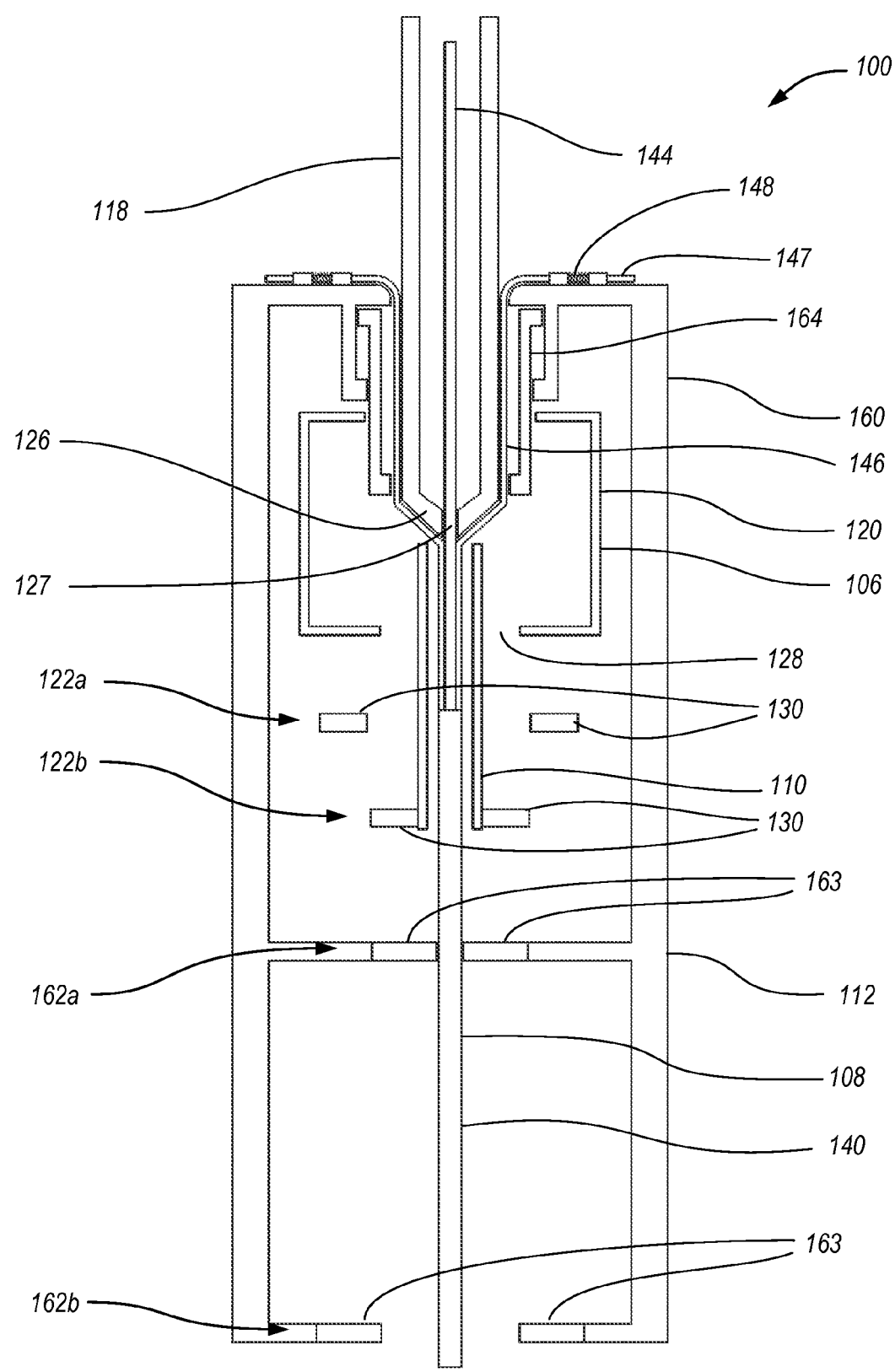
FIG. 2 illustrates an assembled view of the system shown in FIG. 1.

FIGS. 1 and 2 illustrate one embodiment of a system 100 for expanding a medical device 102, such as a vascular device. For ease of reference, a coordinate system will be referenced in discussing system 100 that includes a central axis C, as shown in FIG. 1. Elements that are generally parallel to central axis C will also be described as being longitudinally or axially oriented relative to central axis C while elements that are generally transverse or perpendicular to central axis C will be described as being radially oriented relative to central axis C. In addition, movement parallel to central axis C may be referred to as axial movement. The direction indicated by arrow 104 that is parallel to central axis C will be considered herein as the "distal" direction and the opposite direction will be considered herein as the "proximal" direction. As such, axial movement in the proximal and distal directions may be referred to as proximal and distal movement, respectively. In some embodiments, the distal direction will correspond to vertically "up" and the proximal direction will correspond to vertically "down," and may alternatively be referred to as such.

In addition, to clarify the discussion, when specifically referring to medical device 102 in the expanded state, the identifier 102' may be used.

As shown in the schematic representation of FIG. 1, system 100 can include a support structure assembly 106, an advancement guide assembly 108, a transport assembly guide 110, a transport driver assembly 112, and an advancement mechanism 114.

Support structure assembly 106 comprises a support structure 116 having attached thereto (as schematically represented by solid lines), an expander 118, a thermal chamber 120 and a pair of securing devices 122 (122a and 122b). Expander 118, thermal chamber 120, and securing devices 122 are secured to support structure 116 so as to remain substantially stationary when other portions of system 100 are moved. Support structure 116 can comprise a rack or any other type of rigid support structure that can provide support to expander 118, thermal chamber 120, and securing devices 122 during the use thereof.

Although discussion herein refers to support structure 116 and those items attached to it remaining substantially stationary while other portions of system 100 are moved, this should not be limiting. For example, in some embodiments, support structure 116 can be the portion of system 100 that moves while other portions remain substantially stationary.

Expander 118 is used to expand medical device 102 by forcing medical device 102 radially outward as medical device 102 moves distally with respect to expander 118.

Expander 118 can comprise a distal portion 124 and a conical or frustoconical portion 126 extending proximally from the proximal end of distal portion 124.

In the depicted embodiment, the diameter of distal portion 124 remains substantially unchanged along the entire length of distal portion 124 such that distal portion 124 is substantially cylindrical. However, if desired the diameter of distal portion 124 can instead vary along the length thereof. For example, in one embodiment, the diameter of distal portion 124 decreases as distal portion 124 extends proximally towards conical portion 126 causing distal portion to be tapered. Other shapes are also possible.

Conical portion 126 proximally tapers from the diameter at the proximal end of distal portion 124 to a diameter that can be the same or smaller than the diameter of the unexpanded medical device 102. In some embodiments, conical portion 126 can proximally taper to a diameter that is slightly greater than the diameter of the unexpanded medical device 102. Conical portion 126 can include an alignment guide 127, such as an aperture extending thereinto, to help in aligning advancement guide assembly 108 therewith. In some embodiments, expander can comprise a mandrel.

Figure 3:
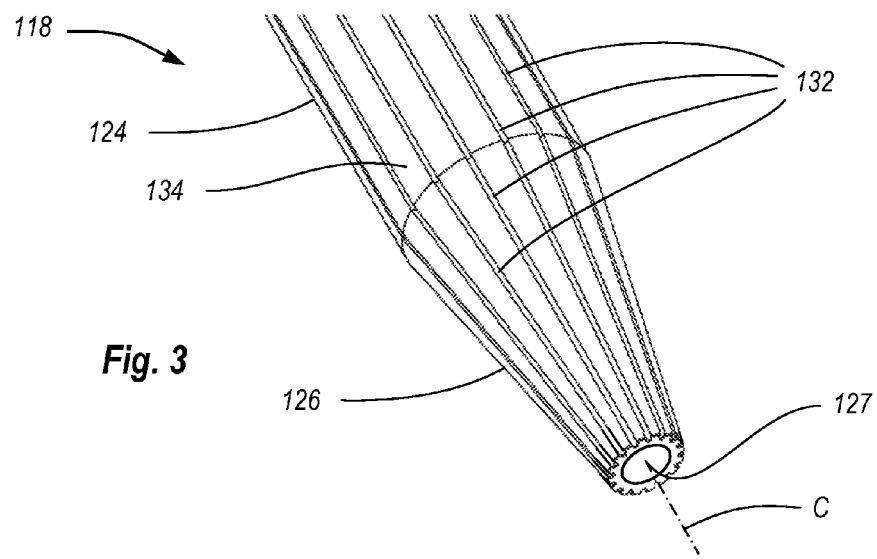
FIG. 3 is a perspective view of an expander according to one embodiment.

If desired, expander 118 can include guides positioned on the outer surface thereof to guide transport mechanisms of advancement guide assembly 108, as discussed below. For example, FIG. 3 shows one embodiment of an expander 118 that has a plurality of transport guides 132 formed on an outer surface 134 of expander 118. Transport guides 132 can be distributed circumferentially about outer surface 134. Each transport guide 132 can extend longitudinally along expander 118 through conical portion 126 and distal portion 124. Transport guides 132 can be configured to receive the transport mechanisms of advancement guide assembly 108 and guide the transport mechanisms as they move axially. Such a configuration can constrain the transport mechanisms and keep them in a particular spatial orientation during expansion of the medical device, thereby allowing for a uniform expansion of the medical device.

Various embodiments of expanders that can be used as expander 118, both with and without transport guides, can be found in U.S. patent application Ser. No. 13/490,225, entitled "APPARATUS, SYSTEMS AND METHODS FOR MEDICAL DEVICE EXPANSION" and filed on the same day as the present application by the present applicant, which is incorporated herein by reference in its entirety. Other expanders, with and without transport guides, can also be used.

Returning to FIG. 1, thermal chamber 120 is used to preheat medical device 102 and to continue to heat medical device 102 as medical device 102 is expanded and heat set. That is, thermal chamber 120 heats medical device 102 to one or more temperatures substantial enough to allow medical device 102 to be expanded from its compressed configuration to its expanded configuration and to heat set medical device 102 in its expanded configuration. Thus, thermal chamber 120 is configured to maintain medical device 102 at predetermined preheat, expansion, and heat set temperatures throughout the preheating, expansion, and heat setting steps.

The predetermined preheat, expansion, and heat set temperatures can be configured to be different from each other or two or all three of the predetermined temperatures can be the same. As such, thermal chamber 120 can be configured to maintain medical device 102 at a same temperature throughout the preheating, expansion, and heat setting steps or to heat medical device 102 to different temperatures for two or three of the steps. If two or more different predetermined temperatures are desired, thermal chamber can be divided axially into two or three sections, each set to a different predetermined temperature so that medical device 120 can be heated to the respective predetermined temperatures as medical device 120 moves axially between the sections during the preheating, expansion, and heat setting steps.

Thermal chamber 120 can have a port 128 at the proximal end of thermal chamber 120 through which medical device 102 can enter and exit chamber 120, and can be large enough to encompass at least the proximal end of expander 118 and a portion of advancement guide assembly 108, as shown. Thermal chamber 120 can comprise any device that can produce and maintain the necessary heat. For example, thermal chamber 120 can comprise any type of oven, such as a natural convection oven, a forced gas convection oven, or the like. Alternatively, thermal chamber 120 can comprise a radio frequency (RF) or microwave heating device, a fluidized heating bed using sand or salt or the like, or any other type of heating chamber.

It is appreciated that thermal chamber is just one example of a means for heating medical device 102. Other means are also possible. For example, in some embodiments, thermal chamber 120 can be omitted and a heating device can be used that directs heat to the medical device and/or the expander 118 without the use of a thermal chamber, such as an RF or microwave heating device. In other embodiments, expander 118 can be heated internally or physically attached to an external heating device so as to be heated by conduction. In still other embodiments, thermal chamber 120 can be used in conjunction with other heating devices, such as an internally heated expander 118. Other combinations are also possible. In sum, although the discussion herein is directed to thermal chamber 120 as the means for heating medical device 102, any apparatus that can be used to heat medical device 102 can be used as the means for heating medical device 102.

Securing devices 122 are used to secure transport assembly guide 110 to support structure 116 yet still allow the expanded medical device 102' to pass over transport assembly guide 110 after medical device 102 has been heat set. To facilitate this, each securing device can selectively open and close at different times so that, during use of system 100, at least one of securing devices 122 is closed to secure transport assembly guide 110. Each securing device 122 can comprise an apparatus, such as a clamp, that selectively secures transport assembly guide 110 to support structure 116. Various types of clamps can be used, as can other types of securing devices that can selectively secure transport assembly guide 110 to support structure 116 while selectively allowing expanded medical device 102' to pass therethrough.

In the depicted embodiment, a pair of clamps 122a and 122b are shown, each having a pair of mating clamp arms 130 that are movable between a clamping position and an open position. In the clamping position, clamp arms 130 secure transport assembly guide 110 therebetween (see, e.g., the position of clamp 122b in FIG. 2); in the open position, assembly guide 110 is free from clamp arms 130 (see, e.g., the position of clamp 122a in FIG. 2). The clamps 122 can be opened and closed in conjunction with one another to secure transport assembly guide 110 to support structure 116 while allowing expanded medical device 102' to pass therethrough. It is appreciated that other numbers of clamps can be used. It is also appreciated that other means of securing transport assembly guide 110 to support structure 106 can alternatively be used.

Continuing with FIG. 1, advancement guide assembly 108 comprises an elongate advancement guide 140 having a transport assembly 142 extending distally from a distal end of advancement guide 140.

Advancement guide 140 is used to longitudinally align medical device 102 with expander 118 as medical device 102 is advanced towards expander 118. Advancement guide 140 can comprise a rod or other type of elongate apparatus that allows medical device 102 to be axially aligned with expander 118 as medical device 102 is advanced towards expander 118, as discussed in detail below.

In addition to axial alignment, advancement guide 140 can also be configured to rotationally align with expander 118. This can be beneficial, e.g., to ensure that transport mechanisms 146 (discussed below) are axially aligned with transport guides 132 of expander 118. Otherwise, undesired torque or other type of stress may be induced on the transport mechanisms when the transport mechanisms are received and/or move within the transport guides during expansion of a medical device, which could have a detrimental effect on the medical device.

In one example, one or more rotational alignment aids can be positioned on advancement guide 140 to ensure that advancement guide 140 is rotationally aligned with expander 118. In one embodiment, the rotational alignment aids can be positioned on advancement guide 140 at the longitudinal location thereof where advancement guide 140 is secured by securing devices 162. For example one or more channels, bores, tracks, flanges or the like can radially extend inward or outward from the surface of advancement guide 140 to engage with mating rotational alignment aids on the securing devices.

Figure 4:
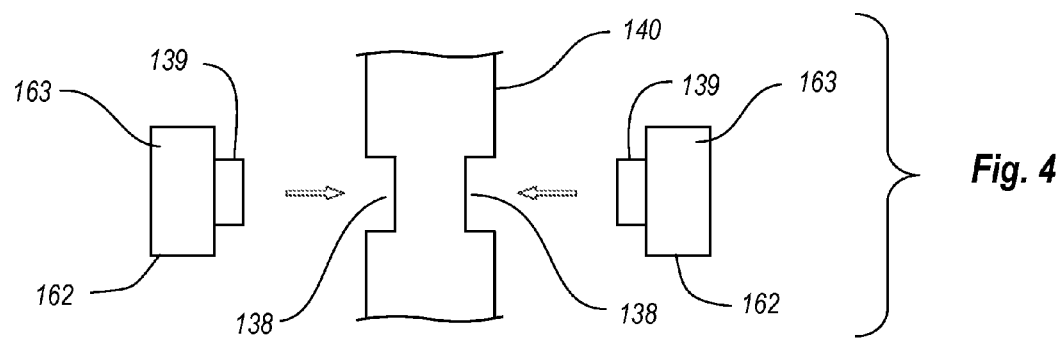
FIG. 4 is a schematic view of a portion of an advancement guide and corresponding securing devices according to one embodiment.

For example, FIG. 4 shows one embodiment of an advancement guide 140 in which a pair of rotational alignment aids 138 in the form of channels or flat spots are positioned on either lateral side of advancement guide 140. Each channel 138 is configured to receive a corresponding mating flange 139 positioned on arms 163 of securing device 162 when securing device 162 secures advancement guide 140. To become fully engaged with each other, channel 138 and corresponding flange 139 can require a particular rotational alignment with each other.

As a result, when securing device 162 is closed so that clamp arms 163 are clamped onto advancement guide 140 and flanges 139 are received within channels 138, flanges 139 can cause advancement guide 140 to rotate to the desired aligned position if advancement guide 140 is out of rotational alignment. Examples of rotational alignment aids that can be used in the present invention can be found in U.S. patent application Ser. No. 13/490,225, cited above. Other types of rotational alignment aids can also be used.

Returning to FIG. 1, transport assembly 142 can be used to receive medical device 102 from advancement guide 140 and to transport medical device 102 over conical portion 126 of expander 118 and to distal portion 124. Transport assembly 142 can be attached to or integrally formed with the distal end of advancement guide 140.

Transport assembly 142 can comprise an axial guide 144 extending distally from advancement guide 140 to axially align transport assembly 142 with expander 118. Axial guide 144 is configured to engage with expander 118. In one embodiment, axial guide 144 comprises a rod or the like that is received within alignment guide 127 within conical portion 126 of expander 118.

Transport assembly 142 can also comprise a plurality of transport mechanisms 146, extending distally from advancement guide 140. Transport mechanisms 146 can be used to provide a bearing-type surface for medical device 102 and to separate at least a portion of medical device 102 from expander 118 during the expansion process to reduce or even eliminate friction between medical device 102 and expander 118. The number of transport mechanisms 146 can vary. The transport mechanisms 146 can comprise wires, strips, ribbons, yarns, threads, rods, or other structures having the desired strength and rigidity, with associated flexibility and resiliency to allow the structure to perform the intended function of transport mechanisms 146. Using materials that can sustain high temperatures can allow the medical device to be heat treated while on the transport mechanisms.

Figure 5:
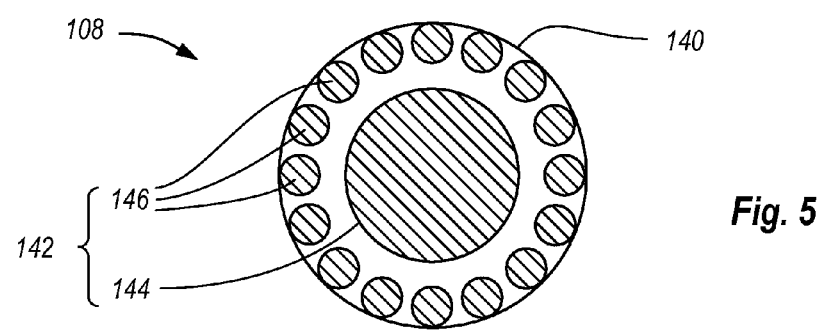
FIG. 5 is a cross sectional view of one embodiment of an advancement guide assembly, taken along section line 5-5 of FIG. 1.

Transport mechanisms 146 can be circumferentially positioned about axial guide 144, if axial guide 144 is used. For example, FIG. 5 shows a cross sectional end view of one embodiment of transport assembly 142 extending from advancement guide 140. In the depicted embodiment, each transport mechanism 146 comprises a wire, and the wires 146 are positioned circumferentially about axial guide 144. The wires can be made of metals or alloys, such as, but not limited to, stainless steel, titanium, tantalum, tungsten, or alloys thereof, nickel chromium (commonly known as nichrome), quartz, glass, glass thread, polymers, or other high temperature material.

As discussed above, a plurality of corresponding transport guides 132, such as recesses, grooves, channels, or the like, can be circumferentially positioned on expander 118, as shown in FIG. 3, to receive transport mechanisms 146 and keep transport mechanisms 146 uniformly spaced circumferentially around expander 118. Transport mechanisms can be sized to project above outer surface 134 of expander 118 when received in transport guides 132.

As a result, medical device 102 can rest on transport mechanisms 146, and move with transport mechanisms as medical device 102 is moved over expander 118. As such, transport mechanisms 146 can provide a separation between medical device 102 and expander 118 to reduce friction that may otherwise occur between medical device 102 and expander 118 during expansion or manufacture of medical device 102. Because of the reduced friction, medical device 102 can be expanded with less susceptibility to adverse effects such as compression, tension, fracturing, bending, uneven expansion, and the like.

Furthermore, because transport guides 132 can be uniformly spaced circumferentially around expander 118, transport mechanisms 146, which slide within transport guides 132, can ensure that medical device 102 remains in a desired rotational orientation when medical device is being expanded, thereby preventing undesired torque, tension, and the like while allowing medical device 102 to uniformly expand. Examples of transport mechanisms 146 that can be used in the present invention can be found in U.S. patent application Ser. No. 13/490,225, cited above. Other types of transport mechanisms can also be used.

Returning to FIG. 1, a tensioning mechanism 148, such as a spring or the like, can be positioned at the distal end 147 of each transport mechanism 146, if desired. Tensioning mechanism 148 can be used to bias transport mechanism 146 during use to aid in the expansion of medical device 102. Tensioning mechanism 148 can comprise a spring or other means of providing a tension to transport mechanism 146 after transport mechanism 146 has been attached to a structure.

Transport assembly guide 110 is used to position transport mechanisms 146 at the proximal end of expander 118. Transport assembly guide 110 can comprise a tubular body with an inside surface 154 having a diameter sized to allow unexpanded medical device 102 to pass inside therethrough and an outside surface having a diameter sized to allow expanded medical device 102' to pass thereover.

As noted above, transport mechanisms 146 can be configured to be received within transport guides 132 on expander 118 and extend axially along expander 118. As such, transport mechanisms 146 expand radially outward as they pass over conical portion 126 to the expanded diameter of distal portion 124. To prevent transport mechanisms 146 from expanding outward before they are received within the transport guides 132, transport mechanisms 146 can pass through transport assembly guide 110. The distal end of transport assembly guide 110 can be positioned adjacent conical portion 126 of expander 118. As such, the inner surface 154 of transport assembly guide 110 can cause transport mechanisms 146 to remain radially in position as transport mechanisms 146 are received within transport guides 132 on expander 118. As noted above, transport assembly guide 110 is secured to support structure 116 by transport assembly guide securing devices 122.

As discussed below, medical device 102 can be positioned within the distal end of transport assembly guide 110 within thermal chamber 120 during preheating of medical device 102. As such, thermal chamber 120 can comprise a metal or other material that can conduct heat. In addition, or alternatively, thermal chamber 120 can be perforated to allow heat to flow into thermal chamber 120. Other types of materials and configurations are also possible for thermal chamber 120.

Transport driver assembly 112 comprises a transport driver 160 having one or more advancement securing devices 162 (162a and 162b) and a transport mechanisms guide 164 attached thereto.

Transport driver 160 is used to move advancement guide assembly 108 distally with respect to support structure assembly 106. Transport driver 160 can comprise a structure that allows advancement guide assembly 108 to be attached thereto and that can move axially with respect to support structure assembly 106.

As discussed above, securing devices 162 are used to secure advancement guide assembly 108 to transport driver 160. Similar to securing devices 122, securing devices 162 are designed to do this, yet still allow the expanded medical device 102' to pass therethrough after medical device 102 has been heat set. As such, securing devices 162 can be similar to securing devices 122, discussed above, and can comprise the same type of apparatuses as securing devices 122. For example, similar to securing devices 122, securing devices 162 can comprise a pair of clamps 162a and 162b each having a pair of mating clamp arms 163 that are movable between a clamping position and an open position.

If one or more rotational alignment aids are positioned along the length of advancement guide 140, securing devices 162 can be configured to secure those rotational alignment aids in a particular rotational configuration to ensure that advancement guide 140 is rotationally aligned in a desired manner, as discussed above. For example, in the embodiment depicted in FIG. 4, each clamp arm 163 of securing device 162 can include a flange 139 configured to be received into channel 138 of advancement guide 140.

Returning to FIG. 1, transport mechanisms guide 164 is used to position transport mechanisms 146 on the distal portion 124 of expander 118. Transport mechanisms guide 164 can comprise a tubular body with an inside surface 166 having a diameter sized slightly larger than the diameter of distal portion 124 so as to constrain transport mechanisms 146 within transport guides 132 on expander 118 when expander 118 is positioned within transport mechanisms guide 164. If distal portion 124 has a diameter that varies along its length, transport mechanisms guide 146 can be designed to resiliently push radially inward so as to follow the contour of distal portion 124.

As noted above, transport mechanisms 146 extend radially outward as they pass over conical portion 126 to the expanded diameter of distal portion 124. To prevent transport mechanisms 146 from extending further radially outward after they have been expanded to the diameter of distal portion 124 and thereby exit transport guides 132 (FIG. 3), transport mechanisms 146 can pass through transport mechanisms guide 164. The proximal end of transport mechanisms guide 164 can be positioned at or near the proximal end of distal portion 124 of expander 118. As such, the inner surface 166 of transport mechanisms guide 164 can constrain transport mechanisms 146 to remain radially in position within the transport guides as transport mechanisms 146 extend onto distal portion 124.

Transport mechanisms guide 164 is slidingly secured to support structure transport driver 160 and configured to be axially movable a specified distance with respect to transport driver 160 to allow space on distal portion 124 for medical device 102 to be positioned for heat setting thereof. As perhaps best illustrated in FIG. 1, transport driver 160 includes an annular channel 170 bounded by a proximal flange 174 and a distal flange 176. Transport mechanisms guide 164 has an outwardly extending flange 168 that is received within channel 170 and is limited to be able to axially move only between flanges 174 and 176.

Advancement mechanism 114 is used to advance medical device 102 distally along advancement guide assembly 108 toward expander 118. Advancement mechanism 114 can comprise a tubular device having an inner diameter sized large enough so that advancement mechanism 114 can easily fit over and slide on advancement guide assembly 108 yet sized small enough to be able to contact an end of the unexpanded medical device 102 and selectively advance unexpanded medical device 102 in a distal direction. Advancement mechanism 114 can be removable from advancement guide 140 to allow the unexpanded medical device 102 to be positioned on advancement guide 140, as discussed below. Advancement mechanism 114 may include an outwardly extending flange 172 or the like on the proximal end to aid in the expansion method, as discussed below.

FIG. 2 illustrates the assembled system 100, ready to receive a medical device. Support structure 116 of support structure assembly 106 has been omitted from FIG. 2 for clarity sake. In addition, because a medical device has not yet been positioned on the depicted system 100, advancement mechanism 114 is not yet positioned on advancement guide assembly 140.

To assemble system 100, advancement guide assembly 108 can be positioned on support structure assembly 106 so that the distal ends of axial guide 144 and transport mechanisms 146 can pass through port 128 into thermal chamber 120. Advancement guide assembly 108 can be advanced so that axial guide 144 can enter into alignment guide 127 on conical portion 126 of expander 118 and transport mechanisms 146 can be received within transport guides 132 on expander 118. As advancement guide assembly 108 is distally advanced, transport mechanisms 146 can correspondingly slide distally relative to expander 118 within transport guides 132.

Before or after advancement guide assembly 108 has been positioned within support structure assembly 106, transport assembly guide 110 can be positioned adjacent conical portion 126 of expander 118 so that transport assembly 106 passes therethrough. Transport assembly guide 110 can be secured to support structure 116 by at least one of the securing devices 122. For example, in the depicted embodiment, clamp 122b is in the closed position to secure transport assembly guide 110.

Transport driver assembly 112 can then be positioned so that advancement guide 140 of advancement guide assembly 108 is positioned between clamp arms 163 of each securing device 162 and so that expander 118 and transport mechanisms 146 extend through transport mechanisms guide 164. The distal ends 147 of each transport mechanism 146 can then be attached to the distal end of transport driver 160 by welding, an adhesive, an attachment device, or any other attachment method or device known in the art.

To keep transport mechanisms 146 taut throughout the medical device expansion process, a tension can be put on transport mechanisms 146 once transport mechanisms 146 have been attached to transport driver 160. For example, advancement guide 140 can be retracted proximally after transport mechanisms 146 are attached to transport driver 160, which can cause tensioning mechanism 148 to place a tension on each transport mechanism 146. Thereafter, advancement guide 140 should be secured by at least one of the advancement securing devices 162 or the tension on transport mechanisms 146 may cause advancement guide 140 to move distally with respect to the tensioning mechanisms 148, thereby releasing the tension. Securing devices 162 can engage rotational alignment aids 138, if the rotational alignment aids are included on advancement guide 140.

To aid in maintaining tension on transport mechanisms 146, each securing device 162 can be dead-weighted, if desired. That is, each securing device 162 can be attached to a weight or other device configured to cause a force on the securing device that is in the opposite direction as the force causing the tension.

Various types of medical devices can be expanded using the systems discussed and envisioned herein. For example, various types of stents and scaffolds can be expanded using the systems discussed and envisioned herein. In one embodiment, medical device 102 can include a material made from any of a variety of known suitable materials, such as a shape-memory material ("SMM") or superelastic material. For example, the SMM can be shaped in a manner that allows for restriction to induce a substantially tubular, linear orientation while within a delivery shaft (e.g., delivery catheter or encircling an expandable member), but can automatically retain the memory shape of the medical device once extended from the delivery shaft. SMMs can be shape-memory alloys ("SMA") or superelastic metals comprised of metal alloys, or shape-memory plastics ("SMP") comprised of polymers.

Examples of SMAs that can be used in medical device 102 include, but are not limited to: copper-zinc-aluminum; copper-aluminum-nickel; nickel-titanium ("NiTi") alloys known as nitinol; and cobalt-chromium-nickel alloys or cobalt-chromium-nickel-molybdenum alloys known as elgiloy. For example, the primary material of the medical device 102 can be of a NiTi alloy that forms superelastic nitinol. Additional materials can be added to the nitinol depending on the desired characteristic.

Examples of SMPs that can be used in medical device 102 include, but are not limited to: biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

FIGS. 6-14 illustrate one embodiment of a method of expanding medical device 102 using system 100. As with other method embodiments discussed or envisioned herein, while an exemplary order of steps will be described in expanding the medical device, it will be appreciated that the steps may be performed in different orders, that additional steps may be included, and/or that steps may be omitted.

In addition, reference will be made to proximal and distal portions of various elements as well as directions of movement. In general, the proximal direction is "down" when viewing FIGS. 6-14, as indicated by arrow 200 on FIG. 6, while the distal direction is "up", as indicated by arrow 202. System 100 can be configured to operate in a vertical configuration, in which the distal direction corresponds to vertically up, although this is not required.

Before expanding a medical device, the medical device must first be initially cut out or otherwise formed. For example, the medical device can be laser cut from a tube having a diameter that is approximately equal to the desired diameter of the compressed (i.e., unexpanded) medical device. The tube can then be deburred to clean any imperfections due to the cutting. Other initial forming methods may also be used.

Before a first medical device is expanded, thermal chamber 120 can be initially energized and allowed to arrive at the desired temperature or temperatures. The desired temperature(s) is/are whatever temperature(s) facilitate expansion and heat setting of the medical device. This can be affected by the material of the medical device among other factors. As noted above, thermal chamber 410 can be configured to maintain medical device 102 at a same predetermined temperature throughout preheating, expansion, and heat setting of medical device 102 or to heat medical device 102 to different predetermined temperatures for two or three of the steps. In one embodiment, the thermal chamber can be between about 450° C. to about 600° C. Of course, other temperature ranges can also be used. Once heated to the desired temperature or temperatures, thermal chamber 120 can be configured to maintain the desired temperature(s) so that the elements remaining therein, such as portions of the expander 118, the transport mechanisms 146, and the transport assembly guide 110, remain heated, even between expansions of different medical devices. This can save significant time and energy compared with conventional medical device expansion approaches.

Also before expanding the medical device, securing devices 122 and 162 should be initially configured as desired. For example, if clamps are used as the securing devices, the clamps should be opened or closed to arrive at the desired initial configuration. Many different initial configurations are possible. For example, in the depicted embodiment, securing devices 122a and 122b are in the open and closed positions, respectively, and securing devices 162a and 162b are in the closed and open positions, respectively. Although various initial configurations are possible, at least one of securing devices 122 and at least one of securing devices 162 should be in the closed position to ensure that transport assembly guide 110 and advancement guide 140 are secured in place in their desired positions relative to one another and relative to expander 118.

Figure 6:
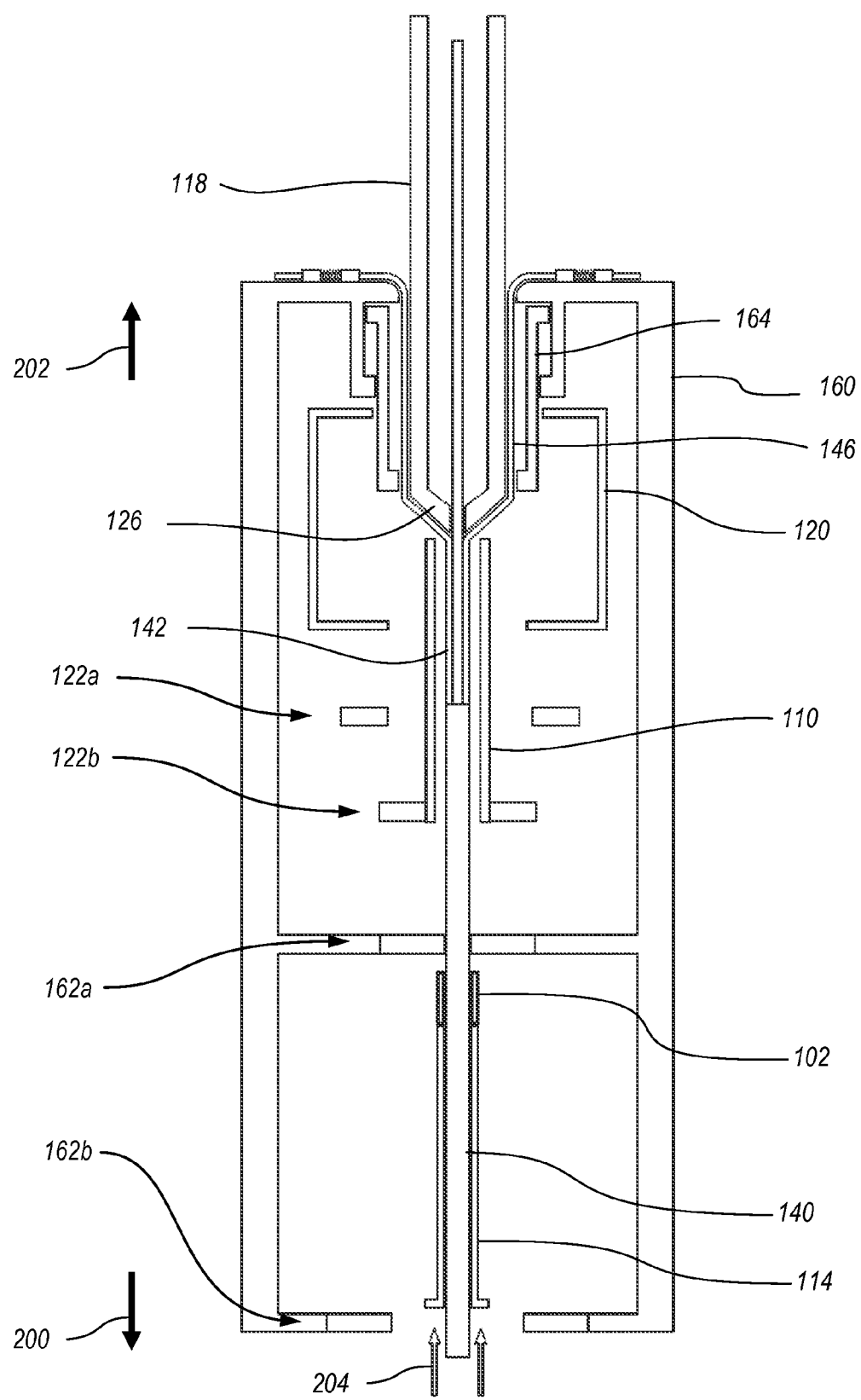
FIGS. 6-14 illustrate various steps of a method for expanding a medical device using the system shown in FIGS. 1 and 2, according to one embodiment.

As shown in FIG. 6, the process can begin by positioning medical device 102 on the system. To do so, securing device 162b is opened, if it is not already in the open position, and medical device 102 is slid onto the proximal end of advancement guide 140, followed by advancement mechanism 114. Thereafter, advancement guide 140 can be advanced distally, as indicated by arrows 204, to push and thereby advance medical device 102 distally. As noted above, to ensure that advancement guide 140 is secured in place, at least one of the securing devices 162a or 162b should be in the closed position. Therefore, securing device 162a should be closed, if it is not already in the closed position, before clamp 162b is opened to secure advancement guide 140.

Figure 7:
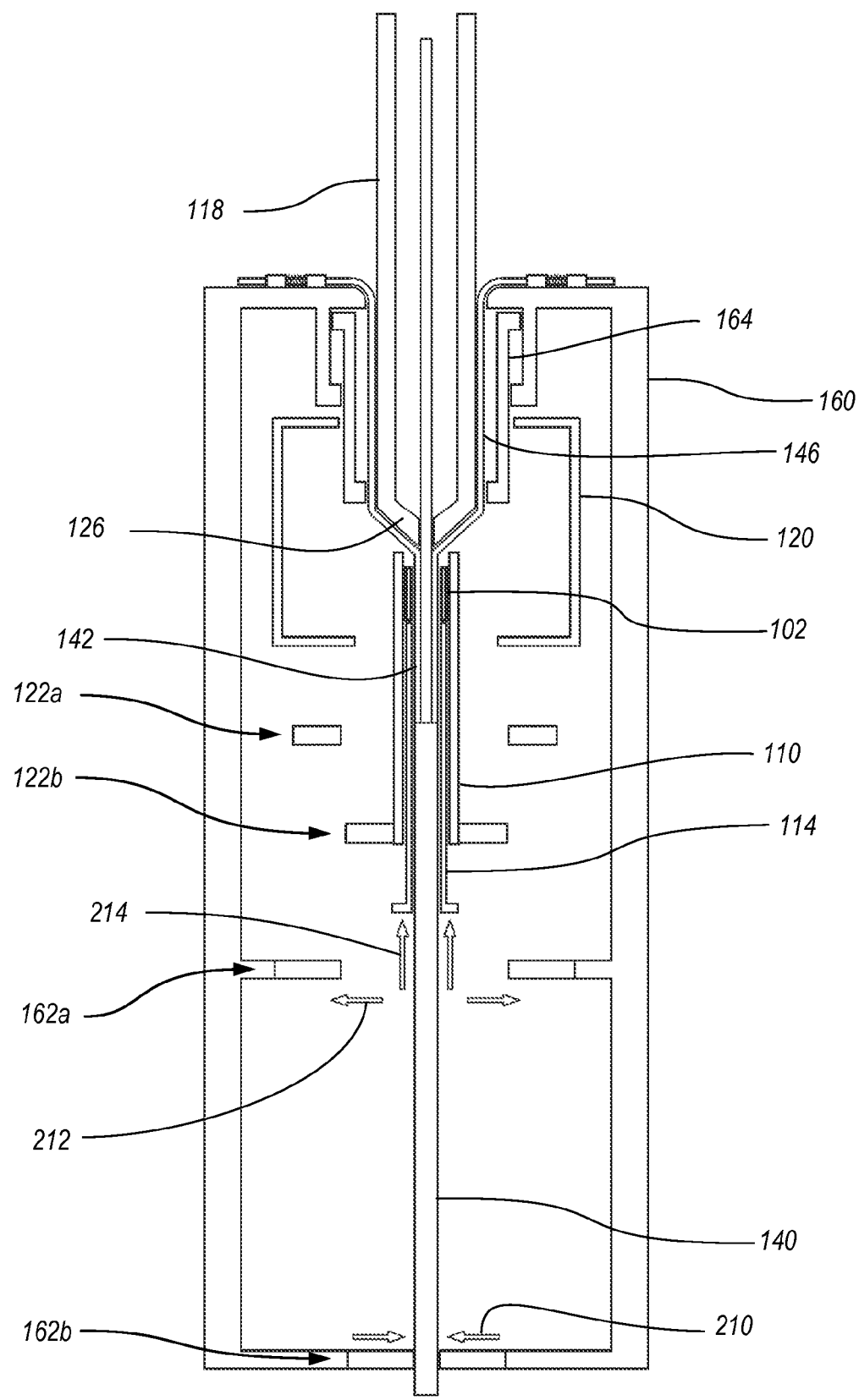

Turning to FIG. 7, once medical device 102 and advancement mechanism 114 are positioned on advancement guide 140, securing device 162b can be closed, as indicated by arrows 210 to secure advancement guide 140, and securing device 162a can then be opened, as indicated by arrows 212. With securing device 162a open, advancement mechanism 114 can be advanced further distally, as indicated by arrows 214, to advance medical device 102 into transport assembly guide 110 and onto the proximal end of transport assembly 142. Advancement mechanism 114 can be advanced distally until the distal end of medical device 102 is positioned adjacent the distal end of transport assembly guide 110.

A guide scale (not shown) can be positioned on the outside surface of the proximal end of transport assembly guide 110, if desired, to help the user know when medical device 102 has arrived at the desired location. Based on the known lengths of medical device 102 and transport assembly guide 110, the user can know before beginning the expansion process how much of advancement mechanism 114 is required to be positioned inside transport assembly guide 110 for medical device 102 to be positioned at the distal end of transport assembly guide 110. The scale can be used to determine when advancement mechanism 114 has been inserted the appropriate distance into transport assembly guide 110. For an automated process, an actuator or the like can be used to advance advancement mechanism 114 the desired distance. Other options are also possible.

When medical device 102 is positioned adjacent the distal end of transport assembly guide 110 as shown in FIG. 7, medical device 102 can be located within thermal chamber 120. As such, medical device 102 can begin to be heated by thermal chamber 120 so as to preheat medical device 102 to the predetermined preheat temperature before expansion is performed. The amount of time it takes for medical device 102 to become preheated to the desired temperature is dependent on many factors. For example, the type of thermal chamber 120, and the thickness, mass and material content of medical device 102, are just a few of the variables that may affect the amount of time required.

However, as noted above, the proximal end of expander 118, the distal end of transport assembly guide 110, and a portion of transport assembly 142 can remain within thermal chamber 120 during the entire expansion process. As such, those devices can remain at the desired temperature(s) and facilitate a relatively quick transition by medical device 102 to the desired temperature(s). That is, the only portion within thermal chamber 120 that is not already heated is medical device 102, and because medical device 102 typically has very little mass, medical device 102 can become heated quickly.

Figure 8:
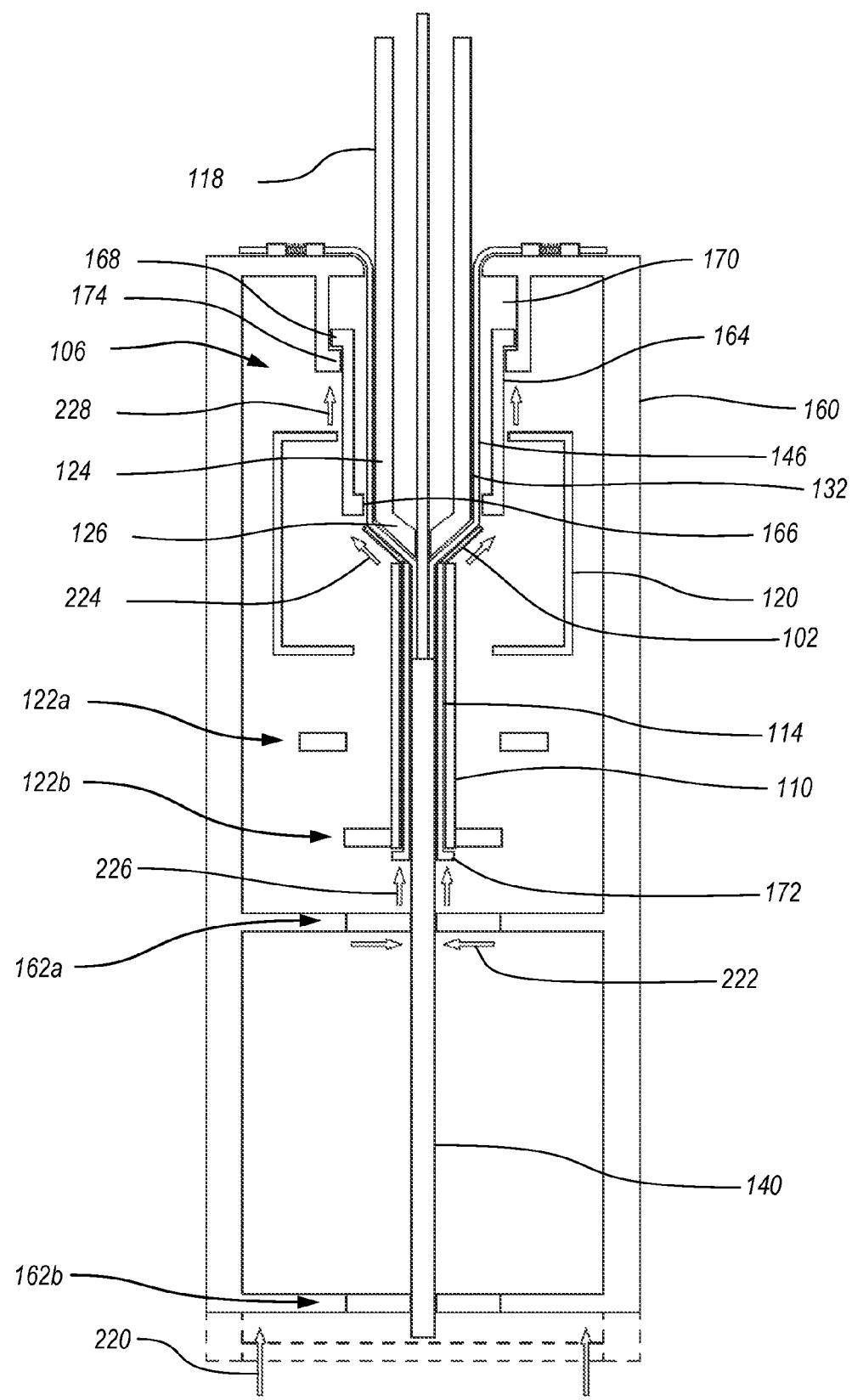

Turning to FIG. 8, once medical device 102 has been preheated to the predetermined preheat temperature, medical device 102 can be uniformly expanded using expander 118. To do so, transport driver 160 can be advanced distally relative to support structure assembly 106, as indicated by arrows 220. Because advancement guide 140 is secured to transport driver 160 by securing device 162b, the distal movement of transport driver 160 also advances guide 140 distally relative to support structure assembly 106. If desired, securing device 162a can also be closed before movement of transport driver 160, as indicated by arrows 222, to further secure advancement guide 140 to transport driver 160. However, this is not required. As noted above, only one securing device 162a or 162b needs to be closed to secure advancement guide 140 to transport driver 160.

Because transport mechanisms 146 are attached to or integrally formed with advancement guide 140 and attached to transport driver 160, the distal movement of transport driver 160 also advances transport mechanisms 146 distally relative to expander 118. Furthermore, because expander 118, thermal chamber 120, and transport assembly guide 110 can all be secured to support structure 116, those devices can remain stationary relative to transport driver 160 when transport driver 160 moves. Thus, when transport driver 160 moves distally, it, along with advancement guide 140 and transport mechanisms 146 move distally relative to expander 118, thermal chamber 120, and transport assembly guide 110.

As a result, as transport driver 160 is advanced distally, transport mechanisms 146 move distally along transport guides 132 on expander 118. As transport mechanisms 146 move along transport guides 132, the portions of transport mechanisms 146 on which medical device 102 is positioned move distally out of the distal end of transport assembly guide 110, then radially outward at conical portion 126, as indicated by arrows 224. As the portions of transport mechanisms 146 distally move, friction between the inner surface of medical device 102 and the outer surface of transport mechanisms 146 draw medical device 102 out of transport assembly guide 110 and onto conical portion 126 of expander 118.

As discussed above, transport mechanisms 146 can act as a bearing-type surface that support and guide medical device 102 while maintaining a separation between medical device 102 and expander 118. As a result, medical device 102 can continue with transport mechanisms 146 as transport mechanisms 146 move radially outward on conical portion 126, with medical device 102 having little or no contact with expander 118. In this manner, transport mechanisms 146 can help reduce or even eliminate frictional engagement between medical device 102 and expander 118. As a result, the likelihood is reduced of damage to medical device 102 from excessive stresses caused by the expander during expansion of the medical device.

During expansion of medical device 110, thermal chamber 120 can maintain medical device 110 at the predetermined expansion temperature. As discussed above, the predetermined expansion temperature can be different than or equal to the predetermined preheat temperature.

To aid in advancing medical device 102 radially outward, advancement mechanism 114 can also be advanced in conjunction with transport driver 160, as indicated by arrows 226, until the distal end of advancement mechanism 114 contacts or becomes adjacent to conical portion 126 of expander 118. Advancement of advancement mechanism 114 can be accomplished by clamping or otherwise temporarily attaching advancement mechanism 114 to advancement guide 140 so that advancement mechanism 114 moves distally with advancement guide 140. In manual systems, advancement mechanism 114 can simply be pressed against advancement guide 140. Of course, other temporary attachment devices and methods can also be used.

To prevent advancement mechanism 114 from distally advancing too far, flange 172 or the like positioned on the proximal end of advancement mechanism 114 can catch on the proximal end of transport assembly guide 110.

As transport driver 160 advances distally, proximal flange 174 also advances distally, as indicated by arrows 228. However, because outwardly extending flange 168 of transport mechanisms guide 164 can move axially within annular channel 170, transport mechanisms guide 164 can remain positioned axially so that inside surface 166 thereof can remain adjacent the proximal end of distal portion 124 of expander 118 when medical device 102 is on conical portion 126. This can help constrain transport mechanisms 146 to remain within transport guides 132 on expander 118.

Figure 9:
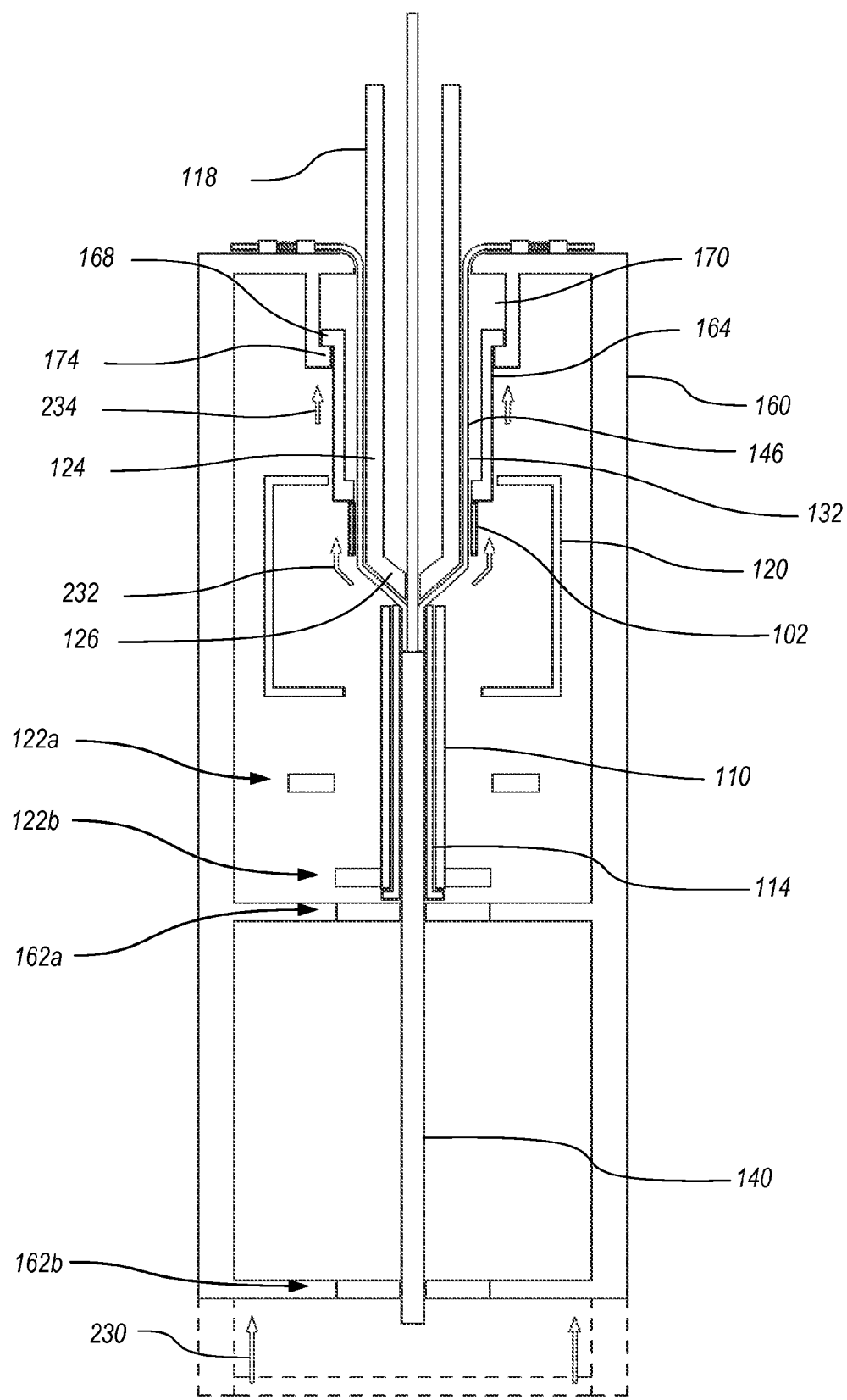

Turning to FIG. 9, further distally advancing transport driver 160 relative to support structure assembly 106, as indicated by arrows 230, causes advancement guide 140 and transport mechanisms 146 to also advance further distally. Because medical device 102 is positioned on transport mechanisms 146, distal and radially outward movement of transport mechanisms 146 can cause medical device 102, due to friction between medical device 102 and transport mechanisms 146, to also move distally and uniformly radially outward, as indicated by arrows 232, until medical device 102 becomes positioned on distal portion 124 of expander 118, as shown in FIG. 9. In this position, medical device 102 is in its expanded configuration.

In the expanded configuration, medical device 110 generally takes on the shape of distal portion 124. For example, in the depicted embodiment, distal portion 124 is substantially cylindrical, thereby causing medical device 110 to also have a substantially cylindrical shape in the expanded configuration. Alternatively, if a tapered medical device is desired, a tapered expander can be used, as discussed above. Because of the tapered shape of distal portion 124, medical device 110 is caused to also have a tapered shape in the expanded configuration. Other expanded medical device shapes can also be obtained by using expanders having distal portions with corresponding shapes.

Just before medical device 102 moves onto distal portion 124, distal movement of transport driver 160 causes proximal flange 174 that bounds channel 170 to bias against and distally push flange 168 of transport mechanisms guide 164. This causes transport mechanisms guide 164 to advance distally, as indicated by arrows 234. The distal movement of guide 164 creates space at the proximal end of distal section 124 of expander 118 for medical device 102 to become positioned thereat. In this manner, the proximal end of transport mechanisms guide 164 can be moved out of the way so that medical device 102 can become positioned on distal portion 124 of expander 118, as illustrated in FIG. 9.

Maintaining transport mechanisms guide 164 as close as possible to the proximal end of distal portion 124 of expander 118 can yield various benefits. For example, transport mechanisms 146 can be constrained to remain within the transport guides on expander 118 at the point where transport mechanisms 146 transition between conical portion 126 and distal portion 124 of expander 118. That is, transport mechanisms guide 164 can constrain transport mechanisms to remain within transport guides 132 at or near the elbow between conical portion 126 and distal portion 124 of expander 118. In conjunction therewith, transport assembly guide 110, through which transport mechanisms 146 pass, similarly constrain transport mechanisms 146 at the proximal end of expander 118 as transport mechanisms 146 transition from transport assembly guide 110 to transport guides 132 on conical section 126 of expander 118.

Medical device 102 can be maintained in the expanded configuration on expander 118 within thermal chamber 120 for a predetermined period of time to heat set the medical device 102. During heat setting of medical device 110, thermal chamber 120 can maintain medical device 110 at the predetermined heat set temperature. As discussed above, the predetermined heat set temperature can be different than or equal to the predetermined expansion temperature and/or the predetermined preheat temperature.

The length of time required to heat set medical device 102 can vary, depending on many factors. For example, a few of the variables that may affect the amount of time required include: the type of thermal chamber 120, the temperature at which medical device 102 is maintained, and the thickness, mass and material content of medical device 102. Of course, other variables may also affect the amount of time required. In one embodiment, the desired heat-set time can vary between 0 seconds (i.e., no time at all) and 15 minutes, or any time therebetween. Other heat-set times are also possible.

Figure 10:
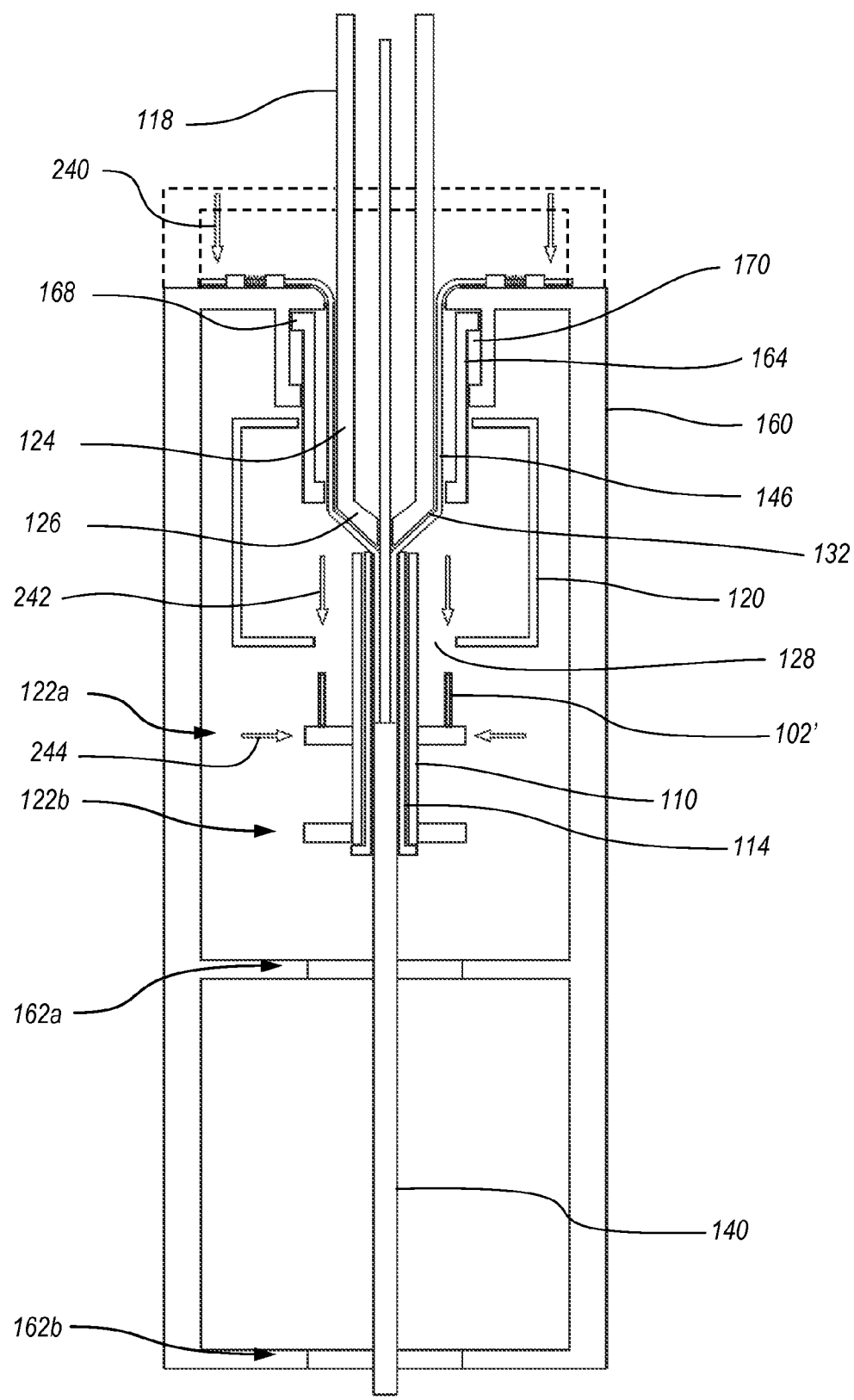

Turning to FIG. 10, after medical device 102 has been expanded and heat set for the predetermined amount of time, the expanded medical device 102' can be removed from the system. To do so, transport driver 160 can be retracted proximally to its original position, as indicated by arrows 240. As transport driver 160 retracts proximally, transport mechanisms 146 and advancement guide 140 also move proximally by virtue of their attachment to transport driver 160.

Transport mechanisms 146 move along transport guides 132 in expander 118 and into transport assembly guide 110 as transport mechanisms 146 move proximally. As such, transport mechanisms 146 follow transport guides 132 as transport guides 132 move radially inward at conical portion 126. The inner wall at the distal end of transport assembly guide 110 can aid in forcing transport mechanisms 146 inward, as noted above. Specifically, as transport mechanisms 146 enter into transport assembly guide 110, the wall at the proximal end of transport assembly guide 110 can provide an inward pressure on transport mechanisms 146, forcing transport mechanisms 146 radially inward.

Because expanded medical device 102' is positioned on transport mechanisms 146 on distal portion 124 of expander 118, proximal movement of transport mechanisms 146 also causes medical device 102' to move proximally. However, instead of following transport mechanisms 146 radially inward at conical portion 126, expanded medical device 102' can remain in its expanded configuration due to the heat setting that has taken place.

As a result, expanded medical device 102' can become disengaged from transport mechanisms 146 at conical portion 126. If system 100 is vertically oriented (i.e., the central axis is oriented vertically), expanded medical device 102' can simply fall in a downward direction (i.e., proximally) due to gravity when medical device 102' becomes disengaged from transport mechanisms 146, as indicated by arrows 242. Due to the expanded configuration, medical device 102' can pass over transport assembly guide 110 and out of thermal chamber 120 through port 128 until medical device 102' comes into contact with one of the securing devices. In the depicted embodiment, securing device 122a has been closed before expanded medical device 102' has become disengaged, as indicated by arrows 244. This can occur anytime before disengagement. As a result, medical device 102' has been stopped and rests upon securing device 122a.

If system 100 is not vertically oriented, means can be included to move expanded medical device 102' proximally. For example, a conveyor belt, a wire, or other type of apparatus can be used. As another example, because medical device 102' is typically very light, a puff of air or other gas can alternatively be used. Other devices and/or methods of moving expanded medical device 102' proximally can also be used. If desired, a track can also be included to guide medical device 102' along its proximal path.

Because expanded medical device 102' is no longer in thermal chamber 120 expanded medical device 102' begins to cool, even as the elements that remain within thermal chamber 120 can remain heated. Before handling expanded medical device 102', it should be allowed to sufficiently cool. To do this, expanded medical device 102' can be allowed to remain at securing device 122a or any of the other securing devices, discussed below, that prevent expanded medical device 102' from being removed from system 100 for a predetermined period of time. Similar to preheating, discussed above, the amount of time required to sufficiently cool expanded medical device 102' can vary, but is typically not long.

As transport driver 160 moves proximally to its original position, annular channel 170 also correspondingly moves proximally. As a result, flange 168 of transport mechanisms guide 164, which is positioned in annular channel 170, also moves proximally, thereby allowing transport mechanisms guide 164 to move to its original position at the proximal end of distal portion 124 of expander 118. If gravity is not sufficient enough to move transport mechanisms guide 164 to its original position, or if system 100 is not vertically oriented, distal flange 176 bounding channel 170 can push proximally on flange 168 to help coax transport mechanisms guide 164 to its original position.

Figure 11:
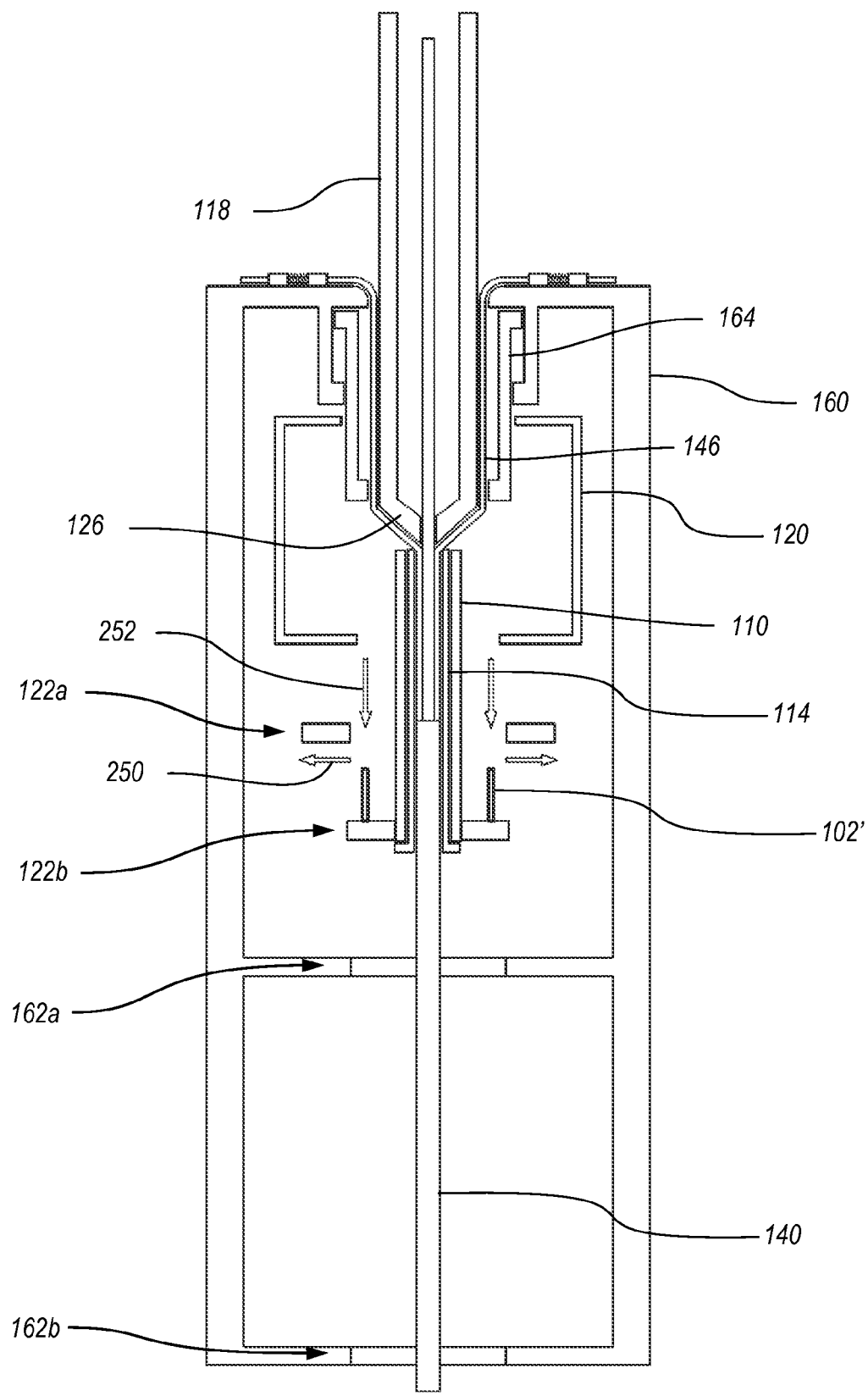

Turning to FIG. 11, securing device 122a can be opened, as indicated by arrows 250, causing expanded medical device 102' to move proximally to securing device 122b, as indicated by arrows 252. Before securing device 122a is opened, however, securing device 122b should be closed, if it hasn't been already, to secure transport assembly 110 while securing device 122a is open.

As noted above, only one of securing devices 122 needs to be closed at any one time to maintain transport assembly guide 110 in its secured position. As such, as long as securing device 122b is closed, securing device 122a can be opened at any time before expanded medical device 102' becomes disengaged from transport mechanisms 146. This can allow expanded medical device 102' to fall directly to securing device 122b without being stopped by securing device 122a, if desired.

Figure 12:
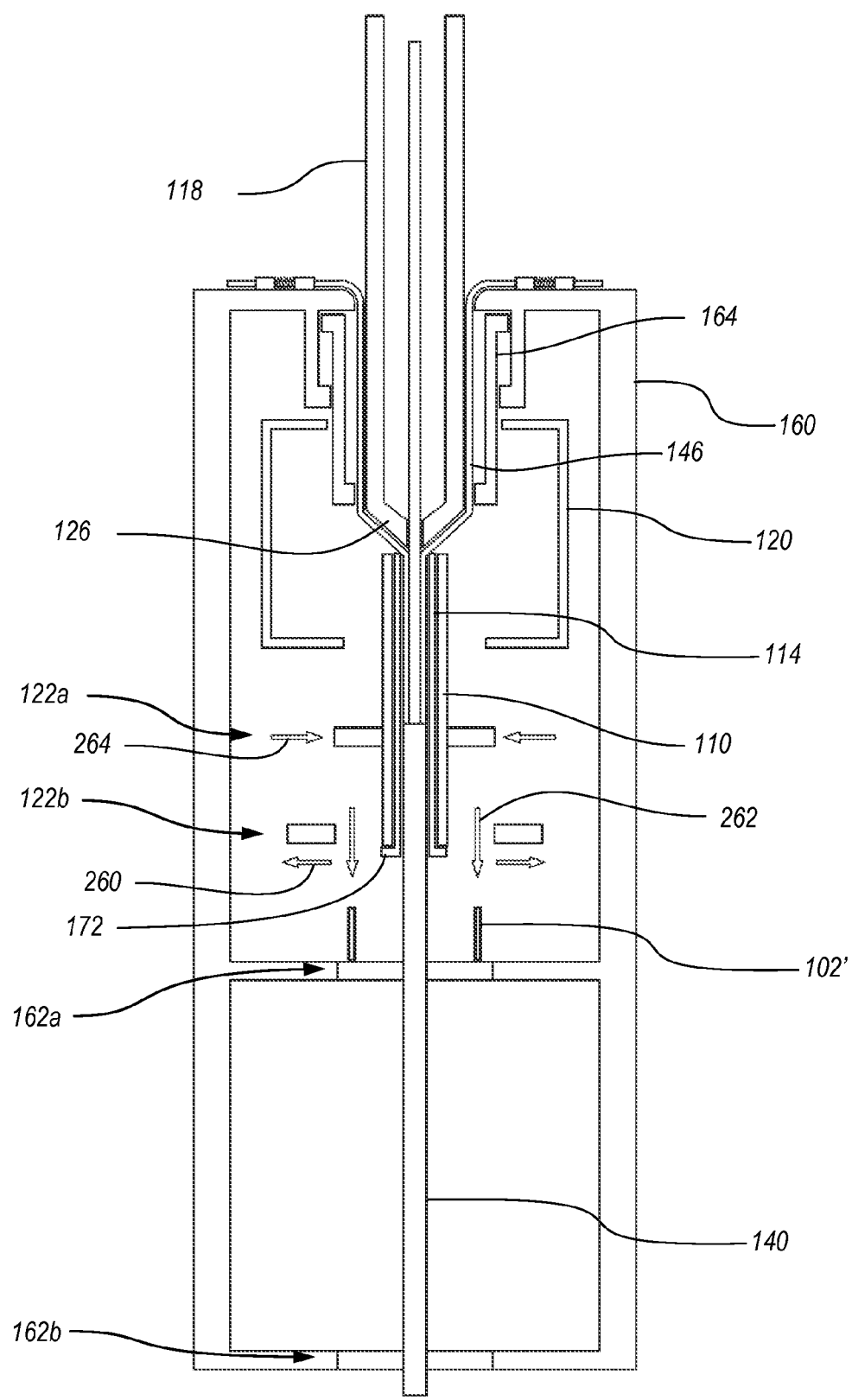

Turning to FIG. 12, securing device 122b can be opened, as indicated by arrows 260, causing expanded medical device 102' to move proximally to securing device 162a, as indicated by arrows 262. Before securing device 122b is opened, however, securing device 122a should be closed, as indicated by arrows 264, to secure transport assembly 110 while securing device 122b is open. If desired, flange 172 at proximal end of transport assembly 110 can be sized radially larger than expanded medical device 102' so that flange 172 prevents medical device 102' from moving proximally past flange 172. In that embodiment, transport assembly 110 must be moved proximally for expanded medical device 102' to continue proximally.

Figure 13:
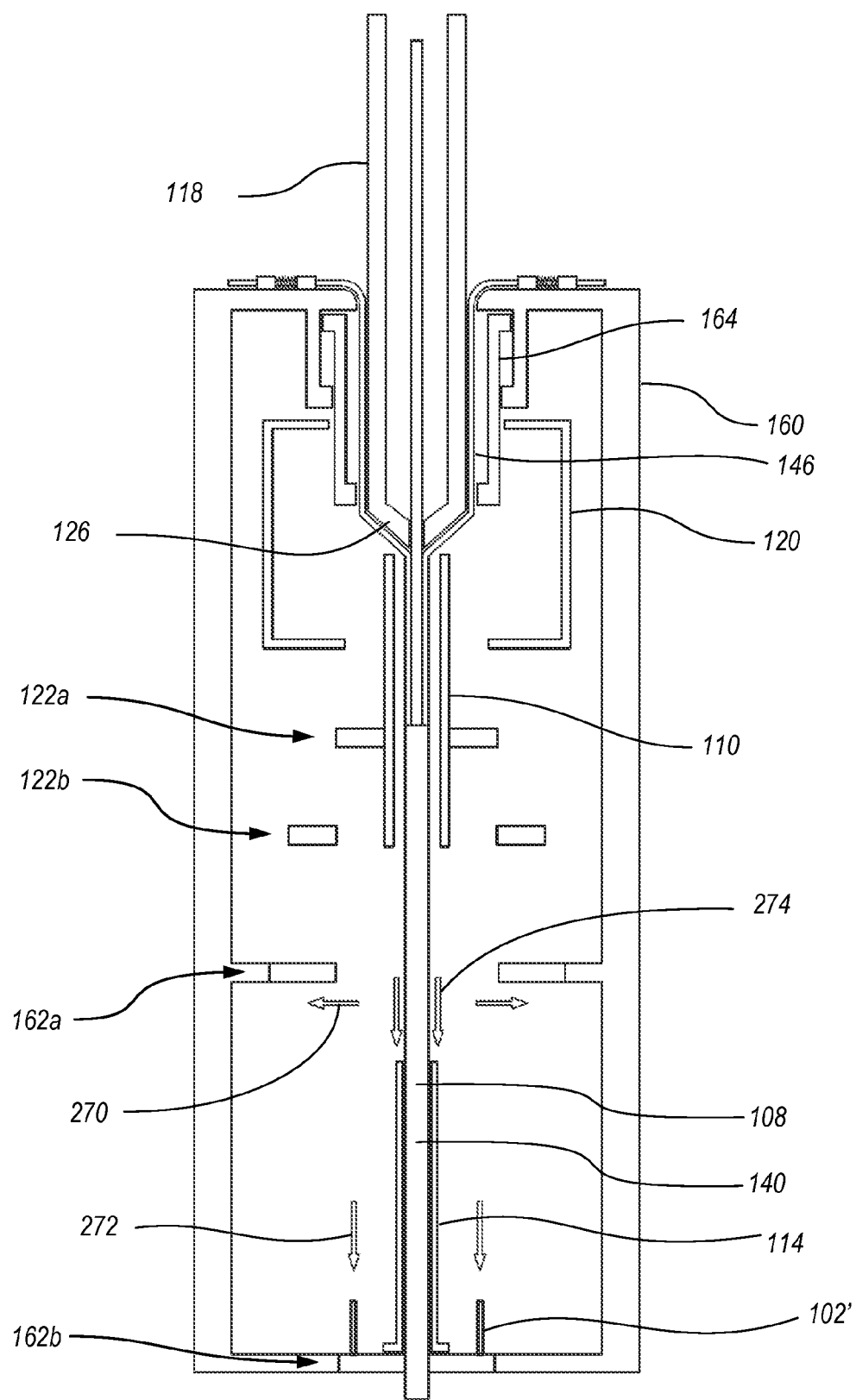

Turning to FIG. 13, securing device 162a can be opened, as indicated by arrows 270, causing expanded medical device 102' to move proximally to securing device 162b, as indicated by arrows 272. In addition, advancement mechanism 114 can also be moved proximally to securing device 162b, as indicated by arrows 274. Before securing device 162a is opened, however, securing device 162b should be closed, if it hasn't been already, to secure advancement guide assembly 108 while securing device 162a is open.

As noted above, only one of securing devices 162 needs to be closed at any one time to maintain advancement guide assembly 108 in its secured position. As such, as long as securing device 162b is closed, securing device 162a can be opened at any time before expanded medical device 102' moves proximally through securing device 122b, if desired. This can allow expanded medical device 102' to fall directly to securing device 162b without being stopped by securing device 162a.

Figure 14:
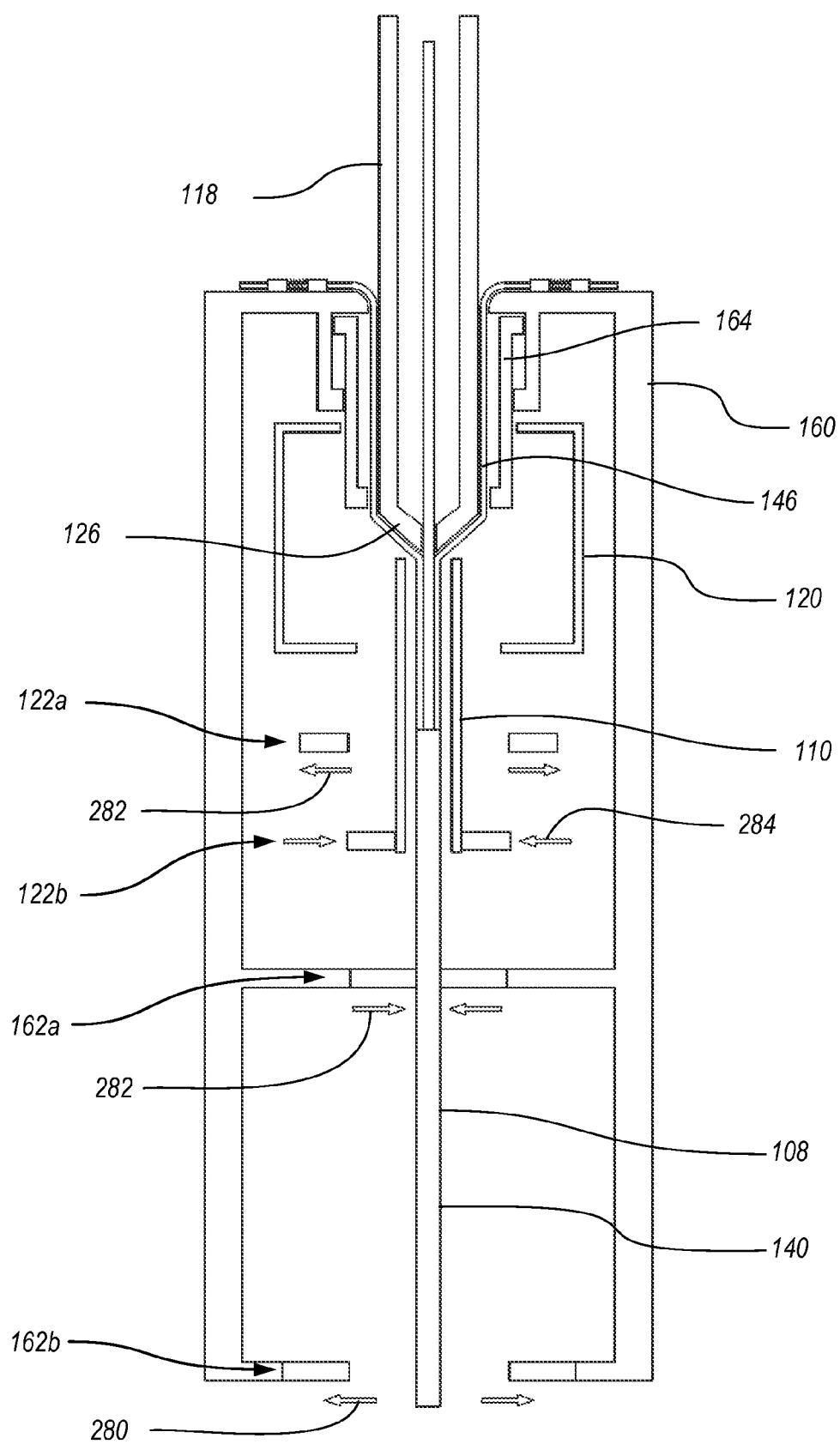

Turning to FIG. 14, securing device 162b can be opened, as indicated by arrows 280, to allow expanded medical device 102' and advancement mechanism 114 to be removed from advancement guide 140. Before securing device 162b is opened, however, securing device 162a should be closed, as indicated by arrows 282, to secure advancement guide assembly 108 while securing device 162b is open.

To ready system 100 to expand another medical device, the elements thereof can be moved to the initial configuration. For example, in the depicted embodiment, securing devices 122a and 122b are respectively opened and closed, as indicated by arrows 282 and 284, to arrive at the initial configuration shown in FIG. 6. Of course, as noted above, other initial configurations are also possible. Care should be taken, however, to make sure that at least one of securing devices 122 and at least one of securing devices 162 are in the closed position at any point in time.

As discussed above, thermal chamber 120 can remain heated throughout the expansion and heat setting processes of medical device 102. In addition, thermal chamber 120 can remain heated during the time between when one expanded medical device is being removed from system 100 and the next unexpanded medical device is being mounted on system 100. As such, thermal chamber 120 can remain heated at a substantially constant temperature while expanding and heat setting a plurality of medical devices, thereby maintaining the proximal portion of expander 118 positioned within thermal chamber 120 at a predetermined temperature for as long as system 100 is in use.

It is appreciated that the systems and methods discussed above can be modified as desired. For example, steps can be added or taken away from the methods, and elements of the system can be modified for a desired use. For example, in one embodiment, the transport guides can be omitted, if desired. In that embodiment, the surface of the expander can be coated with a low-friction material and the transport mechanisms can slide directly on the surface of the expander. However, the transport mechanisms may vary from their rotational positions due to the lack of transport guides. As another example, the transport mechanisms can be omitted, if desired. In that embodiment, the surface of the expander can be coated with a low-friction material and the medical device can slide directly on the surface of the expander and be pushed to the expanded configuration by a modified advancement mechanism. However, the benefits of using the transport mechanisms would be lost.

As another example, the thermal chamber can be filled with an inert gas, such as argon or helium, or a non-inert gas, such as ammonia, so the medical device will not be in contact with oxygen when the medical device is heated. This can prevent oxidation and corrosion from occurring while the medical device is within the thermal chamber. To also prevent oxidation and corrosion from occurring while the medical device is cooling, a cooling chamber full of the inert gas can be positioned adjacent the thermal chamber so that the medical device can move to the cooling chamber directly from the thermal chamber. In that embodiment, securing device 122a can be positioned between the thermal and cooling chamber to act as a door between the chambers, only opening to allow the medical device to pass between the chambers. In this manner, securing device 122a can act as a barrier to prevent the hot gas from heating the cool gas in the cooling chamber and the cool gas from chilling the hot gas in the thermal chamber.

The method described above can be performed manually, can be automated, or can have aspects of both. One of skill in the art would know how to automate such equipment and therefore, with a few exceptions, has not been discussed herein.

The method described above can yield many benefits over conventional systems. For example, because the medical device can be completely expanded at one time without iterating through various expansion sizes, a significant amount of time and energy can be saved compared to the conventional approach.

Furthermore, the portions of the expander and transport assembly on which the medical device is positioned during the preheating and heat-setting steps can be maintained within the thermal chamber. As a result, those portions only need to be brought up to the desired temperature once, when the system is turned on at the first of the day. After that, those portions can be maintained at the desired temperature; no time or energy is wasted in heating those portions after they have cooled off, because those portions are always heated. Because of this, the medical device is the only thing that must be heated each time, and because the medical device is typically very small with little mass, it can quickly arrive at the desired temperature, thereby quickening the process and allowing many medical devices to be expanded per day.

In addition, because the transport mechanisms can act as a bearing-type surface that support and guide the medical device while maintaining a separation between the medical device and the expander, the transport mechanisms can help reduce or eliminate frictional engagement between the medical device and the expander. As a result, the likelihood is reduced of damage to the medical device from excessive stresses caused by the expander during expansion of the medical device.

In addition, the processes can be automated, if desired, to increase the quantity and quality of expanded medical devices. Other benefits may also be possible using the systems and methods discussed and envisioned herein.

The present invention may be embodied in other specific forms without departing from its spirit or essential characteristics. For example, slight modifications of the mandrel are contemplated and possible and still be within the spirit of the present invention and the scope of the claims. The scope of the invention is, therefore, indicated by the appended claims rather than by the foregoing description.

What is claimed is:

1. A method of manufacturing a medical device, the method comprising:
    expanding a medical device by advancing the medical device over a preheated expander, the medical device being uniformly expanded as the medical device is advanced over the preheated expander; and
    heat setting the expanded medical device while the medical device is positioned over the expander, the preheated expander being maintained at a predetermined heat setting temperature after removal of the expanded medical device from the preheated expander,
    wherein uniformly expanding the medical device comprises:
        positioning the medical device on a plurality of transport mechanisms, the transport mechanisms being circumferentially arranged about a central longitudinal axis; and
        advancing the transport mechanisms distally along a plurality of transport guides formed on the preheated expander that cause the transport mechanisms to each move radially outward from the central longitudinal axis as the transport mechanisms advance distally, the medical device being moved distally by the transport mechanisms and the radial outward movement of the transport mechanisms causing the medical device to uniformly expand as the medical device is advanced over the preheated expander.

2. The method recited in claim 1, wherein heat setting the expanded medical device comprises maintaining the expanded medical device over the preheated expander for a predetermined period of time.

3. The method recited in claim 1, wherein the preheated expander is positioned within a thermal chamber that maintains the preheated expander at the predetermined heat setting temperature during the steps of expanding the medical device and heat setting the expanded medical device.

4. The method recited in claim 3, further comprising preheating the unexpanded medical device in the thermal chamber before the medical device is advanced over the preheated expander.

5. The method recited in claim 1, further comprising advancing the medical device towards the preheated expander before expanding the medical device.

6. The method recited in claim 5, wherein advancing the medical device towards the preheated expander comprises positioning the medical device on an advancement guide and advancing the advancement guide towards the preheated expander.

7. The method recited in claim 6, further comprising retracting the advancement guide from the preheated expander to remove the expanded medical device from the preheated expander.

8. The method recited in claim 1, wherein the medical device is physically separated from the preheated expander when the medical device is positioned over the expander.

9. The method recited in claim 1, wherein the medical device is comprised of a shape-memory material.

10. A method of manufacturing a plurality of medical devices, the method comprising:
    performing the method of claim 1 for a first medical device using the preheated expander;
    removing the expanded first medical device from the preheated expander;
    performing the method of claim 1 for a second medical device using the preheated expander; and
    removing the expanded second medical device from the preheated expander, the preheated expander maintaining the heat setting temperature throughout expansion and removal of the first and second medical devices.

11. The method recited in claim 1 further comprising:
    The steps of expanding, heat setting and the removal of the expanded medical device all being performed while the preheated expander is maintained at a predetermined heat setting temperature.

12. The method recited in claim 11, wherein the preheated expander is positioned within a thermal chamber that maintains the preheated expander at the predetermined heat setting temperature during the steps of expanding, heat setting and the removal of the expanded medical device.

13. A method of manufacturing a plurality of medical devices, the method comprising:
performing the method of claim 11 for a first medical device using the preheated expander;
performing the method of claim 11 for a second medical device using the preheated expander, wherein the preheated expander is maintained at the predetermined heat setting temperature throughout expansion and removal of the first and second medical devices.

14. The method recited in claim 1, further comprising removing the expanded medical device from the preheated expander by retracting the transport mechanisms proximally from the preheated expander, thereby causing the medical device to retract proximally from the preheated expander.

15. The method recited in claim 1, wherein the plurality of transport mechanisms comprises a plurality of wires and the plurality of transport guides comprises a plurality of grooves that receive the wires, each groove being sized such that a portion of the wire receive therein extends outward from the groove.

16. The method recited in claim 1, wherein the transport guides are positioned on a conical section of the preheated expander such that the transport mechanisms each move radially outward from a central longitudinal axis of the preheated expander as the transport mechanisms advance distally in the transport guides, thereby causing the medical device to uniformly expand.

\* \* \* \* \*